United States Patent
Armstrong et al.

(10) Patent No.: US 8,833,457 B2
(45) Date of Patent: Sep. 16, 2014

(54) SULFATES AND PHOSPHATES AS ALLOSTERIC EFFECTORS IN MANNANOHYDROLASE ENZYME BREAKERS

(75) Inventors: Charles David Armstrong, Tomball, TX (US); Hoang Le, Spring, TX (US); Bharath Rajappa, Englewood, CO (US); Qi Qu, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 580 days.

(21) Appl. No.: 13/043,349

(22) Filed: Mar. 8, 2011

(65) Prior Publication Data

US 2012/0227971 A1    Sep. 13, 2012

(51) Int. Cl.
  *E21B 43/26* (2006.01)
  *C09K 8/62* (2006.01)
  *C09K 8/68* (2006.01)
  *C09K 8/90* (2006.01)
  *C12N 9/24* (2006.01)

(52) U.S. Cl.
  CPC . *C09K 8/685* (2013.01); *C09K 8/90* (2013.01); *C09K 8/905* (2013.01); C09K 2208/24 (2013.01); *C12Y 302/01078* (2013.01); *C12N 9/2494* (2013.01); *Y10S 507/921* (2013.01)
  USPC ............... 166/308.5; 166/308.2; 507/201; 507/211; 507/921

(58) Field of Classification Search
  USPC ............ 166/308.5, 308.2; 507/201, 211, 921
  See application file for complete search history.

(56) References Cited

U.S. PATENT DOCUMENTS

| | | |
|---|---|---|
| 5,067,566 A | 11/1991 | Dawson |
| 5,165,477 A | 11/1992 | Shell et al. |
| 5,201,370 A | 4/1993 | Tjon-Joe-Pin |
| 5,224,544 A | 7/1993 | Tjon-Joe-Pin et al. |
| 5,226,479 A | 7/1993 | Gupta et al. |
| 5,247,995 A | 9/1993 | Tjon-Joe-Pin et al. |
| 5,421,409 A | 6/1995 | Mueller et al. |
| 5,421,412 A | 6/1995 | Kelly et al. |
| 5,437,331 A | 8/1995 | Gupta et al. |

(Continued)

FOREIGN PATENT DOCUMENTS

| | | |
|---|---|---|
| CA | 2579970 A1 | 8/2008 |
| EP | 0912725 B1 | 7/2004 |

OTHER PUBLICATIONS

Lüthi, E., et al., "Cloning, Sequence Analysis, and Expression in *Escherichia coli* of a Gene Coding for a β-Mannanase from the Extremely Thermophilic Bacterium '*Caldocellum saccharolyticum*'", Applied and Environmental Microbiology; Mar. 1991; pp. 694-700; American Society for Microbilogy.

(Continued)

*Primary Examiner* — Zakiya W Bates
*Assistant Examiner* — Catherine Loikith
(74) *Attorney, Agent, or Firm* — John Wilson Jones; Jones & Smith, LLP (57) ABSTRACT

The allosteric effectors, sulfate and phosphate, can be used with mannanohydrolase enzymes to better control the break of gelled fracturing fluids in wellbore operations. The fracturing fluid contains a hydratable polymer of guar, a guar derivative, a cellulose derivative, a water soluble biopolymer or a combination thereof and a crosslinking agent. The mannanohydrolase enzyme catalyzes the hydrolysis of β-(1,4) mannosidic linkages to break the polymeric backbone.

26 Claims, 5 Drawing Sheets

```
5'
GGATCCATGCGCCTGAAAACCAAAATCCGCAAAAAGTGGCTGTCAGTGCTGTGCAC
TGTAGTCTTTCTGCTGAATATTCTGTTTATTGCGAACGTTACCATCCTGCCAAAAGTA
GGCGCGGCTACCTCCAACGATGGTGTGGTTAAAATTGATACCTCGACCCTGATTGGT
ACCAATCATGCTCATTGCTGGTATCGCGATCGTCTGGATACCGCGCTGCGCGGAATT
CGTAGTTGGGGTATGAACTCGGTACGCGTCGTTCTGTCTAATGGCTATCGCTGGACA
AAAATTCCGGCCAGCGAAGTTGCCAACATTATTTCGCTGTCCCGCTCCCTGGGCTTC
AAAGCCATTATTCTGGAGGTGCATGATACCACCGGTTACGGTGAAGATGGTGCGGC
GTGCTCCCTGGCACAGGCAGTTGAATATTGGAAAGAGATCAAAAGCGTGCTGGATG
GCAATGAAGATTTTGTCATCATCAATATTGGTAATGAACCGTATGGTAATAACAACT
ATCAGAACTGGGTAAATGATACTAAGAATGCAATTAAAGCGCTGCGCGATGCCGGC
TTTAAGCATACCATCATGGTAGATGCGCCGAACTGGGGCCAGGATTGGTCGAATACC
ATGCGCGACAATGCTCAGTCTATTATGGAAGCCGATCCACTGCGTAATCTGGTATTT
AGCATTCACATGTACGGTGTCTATAATACTGCGAGCAAAGTGGAAGAATATATCAA
AAGTTTTGTGGATAAAGGTCTGCCGCTGGTTATCGGCGAATTCGGTCACCAGCACAC
TGATGGTGACCCTGATGAAGAGGCGATCGTTCGCTATGCCAAACAGTATAAAATTG
GCCTGTTTAGTTGGAGTTGGTGTGGGAACAGCAGTTACGTCGGTTACCTGGATATGG
TGAATAACTGGGACCCGAACAACCCGACCCCATGGGGGCAGTGGTATAAAACAAAT
GCGATCGGCACGTCAAGCACGCCGACCCCGACATCGACTGTCACCCCAACGCCACC
GCCGCGCCAGCACCAGCATCGCCAATAAAAGCTT
3'
```

(56) References Cited

U.S. PATENT DOCUMENTS

| | | | |
|---|---|---|---|
| 5,441,109 | A | 8/1995 | Gupta et al. |
| 5,547,026 | A | 8/1996 | Brannon et al. |
| 5,562,160 | A | 10/1996 | Brannon et al. |
| 5,566,759 | A | 10/1996 | Tjon-Joe-Pin et al. |
| 5,806,597 | A | 9/1998 | Tjon-Joe-Pin et al. |
| 5,874,558 | A | 2/1999 | Boel et al. |
| 5,881,813 | A | 3/1999 | Brannon et al. |
| 6,110,875 | A | 8/2000 | Tjon-Joe-Pin et al. |
| 6,138,760 | A | 10/2000 | Lopez et al. |
| 6,186,235 | B1 | 2/2001 | Tjon-Joe-Pin et al. |
| 6,197,506 | B1 | 3/2001 | Fodor et al. |
| 6,197,566 | B1 | 3/2001 | Knap et al. |
| 6,197,730 | B1 | 3/2001 | Kelly et al. |
| 6,566,114 | B1 | 5/2003 | Kauppinen et al. |
| 7,231,976 | B2 | 6/2007 | Berry et al. |
| 7,294,498 | B2 | 11/2007 | Bylina et al. |
| 7,347,265 | B2 | 3/2008 | Monroe et al. |
| 7,392,844 | B2 | 7/2008 | Berry et al. |
| 7,481,273 | B2 | 1/2009 | Javora et al. |
| 8,096,360 | B2 * | 1/2012 | Armstrong ............ 166/300 |
| 2002/0193343 | A1 * | 12/2002 | Khan et al. ............ 514/54 |
| 2003/0203466 | A1 | 10/2003 | Kauppinen et al. |
| 2005/0272612 | A1 | 12/2005 | Dawson et al. |
| 2006/0009363 | A1 * | 1/2006 | Crews ............ 507/100 |
| 2006/0258542 | A1 | 11/2006 | Segura |
| 2007/0270316 | A1 | 11/2007 | El Shaari et al. |
| 2010/0126726 | A1 * | 5/2010 | Armstrong ............ 166/300 |
| 2011/0092397 | A1 * | 4/2011 | Armstrong ............ 507/201 |

OTHER PUBLICATIONS

Daniel D. Morris et al., "Correction of the β-Mannanase Domain of the celC Pseudogene from *Caldocellulosiruptor saccharolyticus* and Activity of the Gene Product on Kraft Pulp", Applied and Environmental Microbiology, Jun. 1995, vol. 61, No. 6, pp. 2262-2269.

Database UniProt [Online] Mar. 24, 2009, "SubName: Full=Mannan endo-1,4-beta-mannosidase., Cellulase; EC=3.2.1.4; EC=3.2.1.78; Flags: Precursor;", retrieved from EBI accession No. UNIPROT:B9MKU6.

Database UniProt [Online] May 1, 2000, "SubName: Full=Multidomain beta-1,4-beta-mannanase; Flags: Precursor;", retrieved from EBI accession No. UNIPROT:Q9RFX5.

Yanhe Ma et al., "Characterization and gene cloning of a novel β-mannanase from alkaliphilic *Bacillus* sp. N16-5", Extremophiles, vol. 8, Springer-Verlag 2004, Aug. 14, 2004, pp. 447-454.

BJ Services Company, "EnZyme G Breakers", Product Information, dated Jul. 28, 2000.

C.D. Armstrong et al., "The Next Generation of Regenerative Catalytic Breakers for Use in Alkaline and High-Temperature Fracturing Fluids", SPE 127936, Society of Petroleum Engineers, 2010 SPE International Symposium and Exhibit on Formation Damage Control, Lafayette, LA, US, Feb. 10-20, 2010, 13 pages.

Charles David Armstrong, U.S. Appl. No. 12/852,915 entitled "Use of Hexose Oxidases to Create Hydrogen Peroxide in Aqueous Well Treatment Fluids" filed Aug. 9, 2010.

* cited by examiner

GGATCCATGCGCCTGAAAACCAAAATCCGCAAAAAGTGGCTGTCAGTGCTGTGCAC
TGTAGTCTTTCTGCTGAATATTCTGTTTATTGCGAACGTTACCATCCTGCCAAAAGTA
GGCGCGGCTACCTCCAACGATGGTGTGGTTAAAATTGATACCTCGACCCTGATTGGT
ACCAATCATGCTCATTGCTGGTATCGCGATCGTCTGGATACCGCGCTGCGCGGAATT
CGTAGTTGGGGTATGAACTCGGTACGCGTCGTTCTGTCTAATGGCTATCGCTGGACA
AAAATTCCGGCCAGCGAAGTTGCCAACATTATTTCGCTGTCCCGCTCCCTGGGCTTC
AAAGCCATTATTCTGGAGGTGCATGATACCACCGGTTACGGTGAAGATGGTGCGGC
GTGCTCCCTGGCACAGGCAGTTGAATATTGGAAAGAGATCAAAAGCGTGCTGGATG
GCAATGAAGATTTTGTCATCATCAATATTGGTAATGAACCGTATGGTAATAACAACT
ATCAGAACTGGGTAAATGATACTAAGAATGCAATTAAAGCGCTGCGCGATGCCGGC
TTTAAGCATACCATCATGGTAGATGCGCCGAACTGGGGCCAGGATTGGTCGAATACC
ATGCGCGACAATGCTCAGTCTATTATGGAAGCCGATCCACTGCGTAATCTGGTATTT
AGCATTCACATGTACGGTGTCTATAATACTGCGAGCAAAGTGGAAGAATATATCAA
AAGTTTTGTGGATAAAGGTCTGCCGCTGGTTATCGGCGAATTCGGTCACCAGCACAC
TGATGGTGACCCTGATGAAGAGGCGATCGTTCGCTATGCCAAACAGTATAAAATTG
GCCTGTTTAGTTGGAGTTGGTGTGGGAACAGCAGTTACGTCGGTTACCTGGATATGG
TGAATAACTGGGACCCGAACAACCCGACCCCATGGGGGCAGTGGTATAAAACAAAT
GCGATCGGCACGTCAAGCACGCCGACCCCGACATCGACTGTCACCCCAACGCCACC
GCCGCGCCAGCACCAGCATCGCCAATAAAAGCTT

MRLKTKIRKKWLSVLCTVVFLLNILFIANVTILPKVGAATSNDGVVKIDTSTLIGTNHAH
CWYRDRLDTALRGIRSWGMNSVRVVLSNGYRWTKIPASEVANIISLSRSLGFKAIILEVH
DTTGYGEDGAACSLAQAVEYWKEIKSVLDGNEDFVIINIGNEPYGNNNYQNWVNDTKN
AIKALRDAGFKHTIMVDAPNWGQDWSNTMRDNAQSIMEADPLRNLVFSIHMYGVYNT
ASKVEEYIKSFVDKGLPLVIGEFGHQHTDGDPDEEAIVRYAKQYKIGLFSWSWCGNSSY
VGYLDMVNNWDPNNPTPWGQWYKTNAIGTSSTPTPTSTVTPTPPPRQHQHRQ*

FIG. 2

GENE SEQUENCING

```
CTCGAGATGAGCAGCGGTTTTTATGTGGATGGTAACACCCTGTATGATGCCAATGGTCAG    60
CCGTTTGTGATGAAAGGCATTAACCATGGCCATGCCTGGTATAAAGATACCCGCGAGCACC   120
GCGATTCCGGCGATTGCCGAACAGGGTGCGAATACCATCCGCATTGTGCTGAGCGATGGT   180
GGCCAGTGGGAAAAAGATGATATTGATACCGTGCGTGAAGTGATCGAACTGGCGGAACAG   240
AATAAAATGGTGGCGGTGGTGGAAAGTTCATGATGCGACCGGTCGCGATAGCCGTAGCGAT   300
CTGGATCGCGCGGTGGATTATTGGATCGAAATGAAAGATGCGCTGATCGGCAAAGAAGAT   360
ACCGTGATTATTAATATTGCGAACGAATGGTATGGTAGCTGGGATGGCGCGGCGTGGGCC   420
GATGGCTATATCGATGTGATTCCGAAACTGCGCGATGCGGGTCTGACCCATACCCTGATG   480
GTGGATGCGGCGGGTTGGGGCCAGTATCCGCAGAGCATTCATGATTATGGTCAGGATGTG   540
TTCAATGCCGATCCGCTGAAAAACACCATCTTTAGCATTCATATGTATGAATATGCGGGC   600
GGTGATGCGAATACCGTTCGCAGCAATATCGATCGTGTGATCGATCAGGATCTGGCCCTG   660
GTTATTGGCGAATTCGGCCATCGTCATACCGATGGCGATGTGGATGAAGATACCATTCTG   720
AGCTATAGCGAAGAAACCGGTACCGGCTGGCTGGCCGTGGAGCTGGAAAGGTAATAGCGCG   780
GAATGGGATTATCTGGATCTGAGCGAAGATTGGGCCCGGCAATCACCTGACCGATTGGGGC   840
AACCGTATTGTGCATGGCGCGAACGGCCTGCAGGAAACCAGCAAACCGAGCACCGTTTTC   900
ACCGATGATAACGGTGGCGCGCCGGAACCGCCGACCACCACCACCCTGTATGATTTTGAA   960
GGCAGCACCCAGGGCTGGCACGGCAGCAACGTGATGGGCGGCCCGTGGAGCGTGACCGAA  1020
TGGGGTGCCAGCGGCAATTATAGCCTGAAAGGCGATGTGAACCTGAGCAGCAACAGCAGC  1080
CACGAACTGTATAGCGAACAGAGCCGTAACCTGCATGGCTATAGCCAGCTGAACGCCGACC  1140
GTGCCGTCATGCGAACTGGGGCAACCCGGGCAATGGCATGAATGCCCGTCTGTATGTGAAA  1200
ACCGGCAGCGATTATACCTGGTATAGCCGGCCCGTTTTACCCGCATCAATAGCAGCAATAGC  1260
GGTACCACCCCTGAGCTTTGATCTGAACAACATCGAAAATAGCCATCACGTGCGCGAAATT  1320
GGCGTTCAGTTTAGCGCCGCGGCGGATAACAGCAGCGGCCAGACCGCGCTGTATGTGGATAAT  1380
GTGACCCTGCGTTAATGATCA                                         1401
```

SULFATES AND PHOSPHATES AS ALLOSTERIC EFFECTORS IN MANNANOHYDROLASE ENZYME BREAKERS

FIELD OF THE INVENTION

The invention relates to gelled fracturing fluids used in wellbore operations. More specifically, the present invention relates to methods of hydrolyzing gelled fracturing fluids using enzymes, whereby the enzymatic activity is regulated using allosteric effectors.

BACKGROUND OF THE INVENTION

Hydraulic fracturing is used to create subterranean fractures that extend from the borehole into the rock formation to improve the rate of production. Generally, a high viscosity fracturing fluid is pumped into the well at sufficient pressure to fracture the subterranean formation. In order to maintain the increased exposure of the formation, a solid proppant may be added to the fracturing fluid, which is carried into the fracture by the high pressure applied to the fluid.

Some conventional fracturing fluids include guar gum (galactomannans) or guar gum derivatives, such as hydroxypropyl guar (HPG), carboxymethyl guar (CMG), or carboxymethylhydroxypropyl guar (CMHPG). These polymers can be crosslinked in order to increase their viscosities and increase their capabilities of proppant transport.

Once the formation is adequately fractured and the proppant is in place, the fracturing fluid is recovered typically through the use of breakers. Breakers generally reduce the fluid's viscosity to a low enough value allowing the proppant to settle into the fracture, thereby exposing the formation to the well. Breakers work by severing the bonds of the polymer. This "breaks" the polymer reducing its molecular weight. The fracture then becomes a high permeability conduit for fluids and gas to be produced back to the well.

Breakers control the timing of the break for the fracturing fluid. Gels that break prematurely can cause suspended proppant material to settle out of the gel before being introduced a sufficient distance into the produced fracture. Also, premature breaking can result in a premature reduction in the fluid viscosity resulting in a less than desirable fracture length in the fracture being created. For purposes of the present application, premature breaking will be understood to mean that the gel viscosity becomes diminished to an undesirable extent before all of the fluid is introduced into the formation to be fractured.

On the other hand, gelled fluids that break too slowly can cause slow recovery of the fracturing fluid and a delay in resuming the production of formation fluids. Additional problems can result, such as the tendency of proppant to become dislodged from the fracture, resulting in an undesirable closing and decreased efficiency of the fracturing operation.

Optimally, the fracturing gel will begin to break when the pumping operations are concluded. For practical purposes, the gel should be completely broken within a specific period of time after completion of the fracturing period. At higher temperatures, for example, about 24 hours is sufficient. A completely broken gel will be taken to mean one that can be flushed from the formation by the flowing formation fluids or that can be recovered by a swabbing operation.

By comparison, certain gels, such as those based upon guar polymers, undergo a natural break without the intervention of chemical additives; however, the break time can be excessively long. Accordingly, to decrease the break time of gels used in fracturing, chemical agents are incorporated into the gel and become a part of the gel itself. Typically, these agents are either oxidants or enzymes that operate to degrade the polymeric gel structure.

Still, obtaining controlled breaks using various chemical agents, such as oxidants or enzymes, is challenging. Oxidants are ineffective at low temperature ranges from ambient temperature to 130° F. They require either higher temperatures to function as breakers or a coreactant to initiate cleavage of the viscosifying polymer. Oxidants do not necessarily break the polysaccharide backbone into monosaccharide units. The breaks are nonspecific, creating a mixture of macromolecules. Further, common oxidants are difficult to control because they not only attack the polymer, but they also react with any other molecule that is prone to oxidation. For example, oxidants can react with the tubing and the linings in the well, or the resins on resin-coated proppants.

In contrast, enzymes, are catalytic and substrate specific, hydrolyzing distinct bonds of the polymer. As a catalyst, they will hydrolyze many polymeric bonds before they eventually degrade. Enzymes can avoid the high temperatures associated with the chemical oxidants. However, they often operate under narrow pH and temperature ranges.

Conventional enzymes used to degrade galactomannans have maximum catalytic activity under mildly acidic to neutral conditions (pH 5 to 7). Activity profiles indicate the enzymes retain little to no activity at higher pH values. Their activity rapidly declines above pH 8, and they begin to denature above pH 9. This can pose a problem, for example, in borate-crosslinked guar gels, because these gels are also pH dependant, generally needing a pH in excess of 8 to initiate the gellation. As the pH increases, the resulting gel becomes stronger. Normally, when enzymes are used with borate-crosslinked gels, the gels are buffered to maintain a pH range of 8.2 to 8.5 to ensure gellation, but to inhibit enzyme degradation. This technique requires high concentrations of both borate and enzyme. Unfortunately, while ensuring good breaks, the initial gel stability and proppant transport capability is weakened. The determination of the optimum enzyme concentration is a compromise between initial gel stability and an adequate break.

Moreover, these enzymes work well at ambient to moderate temperatures (75° F. to 150° F.). At elevated temperatures, (>150° F.) they quickly denature and lose activity. The galactomannans used in conventional enzyme formulations have a temperature maximum of approximately 150° F. Activity profiles indicate that the enzyme retains little to no activity past this point, while many downhole fracturing operations are conducted at temperatures in excess of 150° F.

It would be an important advantage for the well operator to have greater control over the enzyme activity and, hence, the rate of hydrolysis of the polymer, to allow for a more timely and adequate break. Control over the enzyme activity could also allow the well operator to better work within the constraints of pH and temperature, and even allowing for less enzyme to be used fracturing fluid formulations.

SUMMARY OF THE INVENTION

The present invention relates to the use of allosteric effectors to better regulate the activity of the enzyme breakers. It has been discovered that the mannanohydrolase enzymes disclosed in U.S. Pat. No. 8,058,212 and U.S. Pat. No. 8,096,360, hereby incorporated by reference, possess allosteric binding sites. The present invention uses sulfates and phosphates as effectors to better control the break of the fracturing gel containing mannanohydrolase enzymes.

DETAILED DESCRIPTION OF THE PREFERRED EMBODIMENTS

Illustrative embodiments of the invention are described below as they might be employed in the operation and in the treatment of oilfield applications. In the interest of clarity, not all features of an actual implementation are described in this specification. It will of course be appreciated that in the development of any such actual embodiment, numerous implementation-specific decisions must be made to achieve the developers' specific goals, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description.

As an embodiment of the present invention, a method of fracturing a subterranean formation that surrounds a wellbore is provided. In this embodiment, a crosslinked polymer gel is provided that includes an aqueous fluid, a hydratable polymer, a crosslinking agent capable of crosslinking the hydratable polymer, a sulfate or a phosphate, and an enzyme breaker comprising a mannanohydrolase. The crosslinked polymer is then injected to a desired location within the wellbore and into contact with the formation under sufficient pressure to fracture the surrounding subterranean formation. The polymer may be injected after it is fully crosslinked or while the crosslinking is underway. Once the fracturing is complete, the enzyme breaker is allowed to degrade the crosslinked polymer gel so that it can be recovered or removed from the subterranean formation.

Besides the method embodiments, compositions are also provided as embodiments of the present invention. As another embodiment of the present invention, a fracturing fluid composition is provided. The fracturing fluid comprises an aqueous fluid, a hydratable polymer, a crosslinking agent capable of crosslinking the hydratable polymer, a sulfate or a phosphate, and an enzyme breaker comprising a mannanohydrolase.

The enzyme breakers of the present invention preferably comprise mannanohydrolases. In an aspect, the mannanohydrolase enzyme originates from the thermophilic and anaerobic *Caldocellum saccharolyticum*. Isolation of the gene encoding for the mannanohydrolase enzyme is described in E. Luthi et al, "Cloning, Sequence Analysis, and Expression in *Escherichia coli* of a Gene Coding for a β-Mannanase From the Extremely Thermophilic Bacterium '*Caldocellum saccharolyticum*', Applied and Environmental Microbiology, March 1991, pp. 694-700, herein incorporated by reference.

Figure 1A:
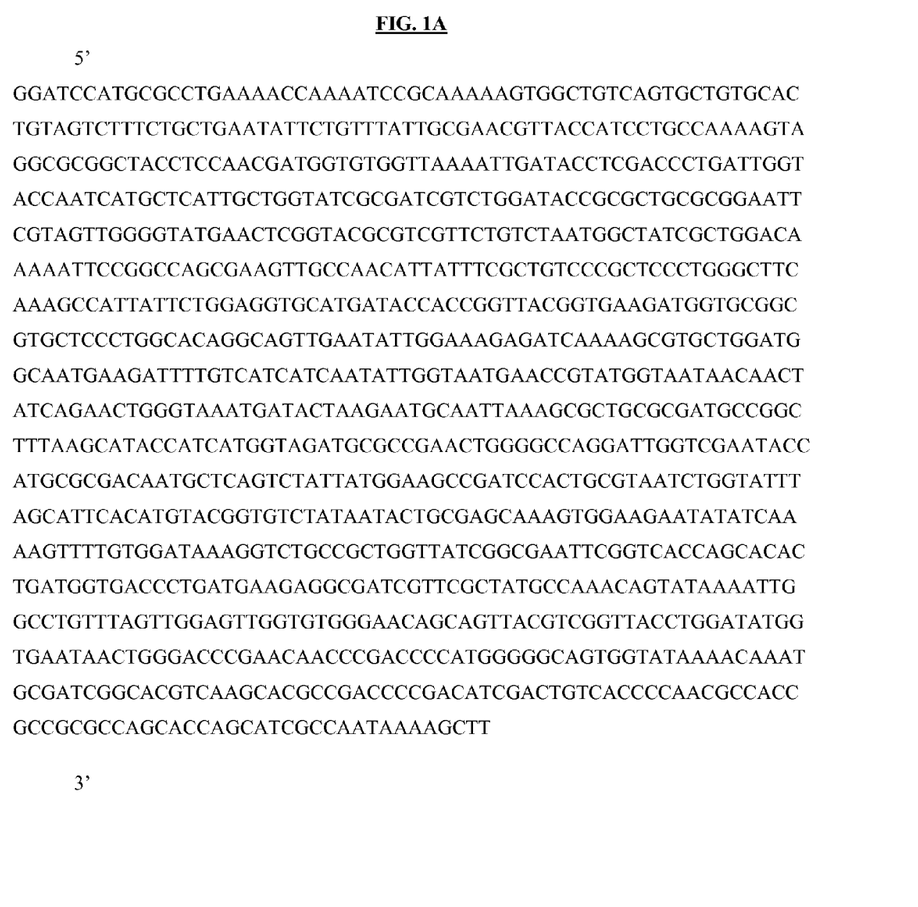
FIG. 1A (SEQ ID NO:1) represents the nucleotide sequence that codes for a mannanohydrolase used in an aspect of the invention.
Figure 1B:
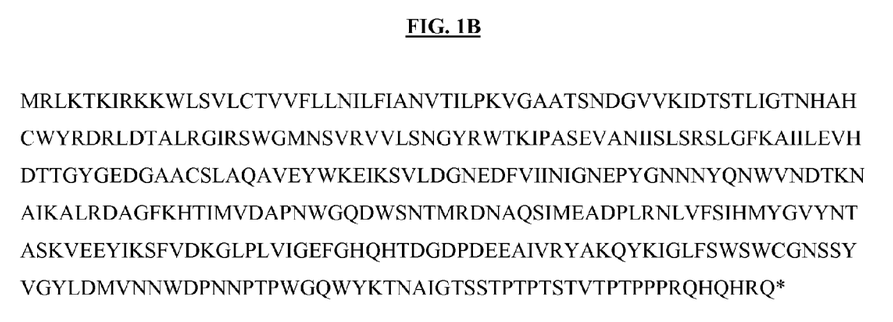
FIG. 1B (SEQ ID NO:2) represents the amino acid sequence of a mannanohydrolase used in an aspect of the invention.

The gene for this mannanohydrolase was codon optimized to increase the efficiency of its expression in *E. coli*, as disclosed in U.S. Pat. No. 8,058,212. The nucleotide sequence of the htβ gene is set forth in FIG. 1A (SEQ ID NO:1), while its corresponding amino acid sequence is set forth in FIG. 1B (SEQ ID NO:2). The nucleotide sequence includes the coding sequence for the mannanohydrolase and the leader sequence on the N-terminus.

Figure 2:
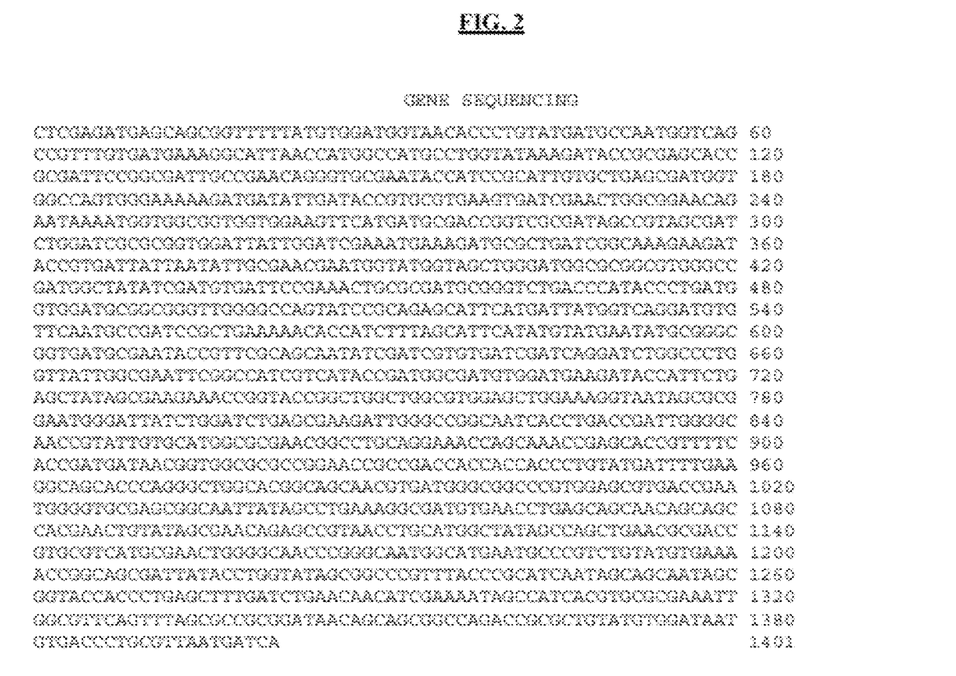
FIG. 2 (SEQ ID NO:3) is the sequence of the gene that is codes for an enzyme breaker made in accordance with embodiments of the present invention.

In another aspect, the enzyme breaker is derived from a gene from the alkaliphilic *Bacillus* sp. N16-5. In an aspect, the enzyme breaker is a member of the glycosyl hydrolase family 5 and is an active β-mannanase. This enzyme breaker can be prepared in accordance with the methods described in U.S. Pat. No. 8,096,360. The nucleotide sequence for the enzyme is shown in FIG. 2 (SEQ ID NO:3). In an aspect, the gene is codon optimized for expression in *E. coli*.

The enzyme breakers of the present invention catalyze the hydrolysis of β-(1,4) mannosidic linkages and can be used to break the polymer backbone of galactomannan polymers.

Generally, reactions take place in the enzyme's active site, which is specifically structured for a particular substrate and chemical reaction. In some cases, other binding sites exist within the enzyme or on its surface. In a process called allosteric regulation an effector molecule can bind to these sites and affect the enzyme activity. Allosteric activators are those molecules that bind to the enzyme and enhance the enzyme's activity against a particular substrate, while allosteric inhibitors decrease the enzyme's activity. It is thought that enzymes with allosteric binding sites exist in two different conformations. One of these conformers will have a lower activation energy for the catalyzed reaction. The binding of an allosteric activator molecule can shift the equilibrium from one conformational state to the other.

It has been discovered that both of the aforementioned mannanohydrolase enzymes possess allosteric activator binding sites for sulfates and phosphates, although other 1,4-β-mannanases are contemplated and within the scope of the present invention. The preferred sulfate or phosphate compounds as the allosteric effectors are those soluble in water and brines. Using such effectors enhances the enzymatic breakdown of the polymer so that the reaction occurs faster, is more efficient and complete, resulting in no rebound of viscosity upon cooling of the breaker fluid. An advantage of the present invention is the ability to control the rate of hydrolysis of the guar polymer. This would give the well operator more control over the rate at which the fracturing fluid broke. Another possible advantage of the present invention is that less enzyme product is needed to achieve a complete break in the viscosity of the polymer. A reduction in the amount of enzyme breaker needed results in a cost savings in terms of enzyme production, shipping, and storage.

The enzyme breaker and the effectors, phosphate and sulfate, may be diluted in various concentrations that are effective and convenient for use in fracturing jobs. In an aspect, the enzyme breaker of the present invention may be diluted to a concentration of about 1:24 and is present in the crosslinked polymer gel in a range of about 0.25 gpt to about 4 gpt of 1/100 dilution: alternatively, in a range of about 0.5 gpt to about 2.5 gpt; alternatively, in a range of about 0.5 gpt to about 1 gpt; or alternatively, in a range of about 1 gpt to about 2 gpt. In an aspect, the total protein concentration of the stock enzyme breaker from which the dilutions are made is greater than 1 mg/mL. Preferably, the effector will be used in about a 1:1 stoichiometric ratio with the enzyme breaker. In an aspect, a 1 gpt of a 20 wt. % aqueous solution of $Na_2SO_4$ is used. But, an aqueous solution of 0.005 wt. % of sulfate or phosphate and greater may also be used. Other suitable dilution concentrations of enzyme breaker and allosteric effector will be apparent to those of skill in the art and are to be considered within the scope of the present invention.

The methods and compositions described herein can be used with a variety of hydratable polymers. In an aspect, the hydratable polymer has repeating units of mannose linked by β-(1,4) mannosidic linkages. In another aspect, the hydratable polymer is a polysaccharide and comprises guar, guar derivatives, cellulose derivatives, water soluble biopolymers, or combinations thereof. GW-3LDF is a particularly suitable guar polymer that is commercially available from Baker Hughes Inc. In an aspect, the intrinsic viscosity of the hydratable polymer in the aqueous fracturing fluid is greater than about 14 dl/g. In another aspect, the intrinsic viscosity of the hydratable polymer in the aqueous fracturing fluid is greater than about 16 dl/g. Other suitable types of hydratable polymers that can be used in the methods and compositions described herein will be apparent to those of skill in the art and are to be considered within the scope of the present invention.

Because some enzyme breakers of the present invention have a maximum activity under alkaline pH ranges, they can be combined with other breakers that operate in different pH ranges to allow for better control of hydrolysis of fracturing fluids over a much greater pH range. In an aspect, the crosslinked polymer gel can further include a second enzyme breaker that is catalytically active and temperature stable in a pH range of about 4 to about 10. Suitable enzymes that can be used include those described in U.S. Pat. No. 5,201,370, which is hereby incorporated by reference.

Divalent cations can affect the activity of the enzyme breaker of the present invention. In an aspect, the crosslinked polymer gel can further include a divalent cation. Suitable divalent cations can include $Mg^{2+}$, $Ca^{2+}$, $Cd^{2+}$, $Ni^{2+}$, $Co^{2+}$, or $Mn^{2+}$. Other suitable divalent cations that can be used in the present invention will be apparent to those of skill in the art and are to be considered within the scope of the present invention.

The methods and compositions described herein can be used with a wide variety of crosslinking agents. A suitable crosslinking agent can be any compound that increases the viscosity of the hydratable polymer by chemical crosslinking, physical crosslinking, or any other mechanisms. For example, the gellation of the hydratable polymer can be achieved by crosslinking the hydratable polymer with metal ions including borate compounds, zirconium compounds, titanium compounds, aluminum compounds, antimony compounds, chromium compounds, iron compounds, copper compounds, zinc compounds, or mixtures thereof. One class of suitable crosslinking agents is zirconium-based crosslinking agents. Suitable crosslinking agents can include zirconium oxychloride, zirconium acetate, zirconium lactate, zirconium malate, zirconium glycolate, zirconium lactate triethanolamine, zirconium citrate, a zirconate-based compound, zirconium triethanolamine, an organozirconate, or combinations thereof. XLW-14 is a particularly suitable zirconate-based crosslinking agent that is commercially available from Baker Hughes Inc. Suitable borate-containing crosslinking agents can include, for example, alkaline earth metal borates, alkali metal borates, borate esters, probertite, ulexite, nobleite, frolovite, colemanite, calcined colemanite, priceite, pateroniate, hydroboractie, kaliborite, or combinations thereof. XLW-32 is a particularly suitable boron-based crosslinking agent that is commercially available from Baker Hughes Inc. Suitable titanium-containing crosslinking agents can include, for example, titanium lactate, titanium malate, titanium citrate, titanium ammonium lactate, titanium triethanolamine, titanium acetylacetonate, or combinations thereof. Suitable aluminum-containing crosslinking agents can include, for example, aluminum lactate, aluminum citrate, or combinations thereof. Other suitable crosslinking agents that are compatible with the compositions and methods described herein will be apparent to those of skill in the art and are to be considered within the scope of the present invention.

The amount of crosslinking agent and other additives used in the present invention can vary depending upon the desired effect of the additives. For example, the crosslinking agent can be present in the crosslinked polymer gel in an amount sufficient to provide the desired degree of crosslinking between molecules within the hydratable polymer. The amounts of additives that can be used in the present invention will be apparent to those of skill in the art and are to be considered within the scope of the present invention.

Besides the polymers, crosslinking agents, effectors, and enzyme breakers, various additives can be useful in the present invention. Additives used in the oil and gas industry and known in the art, including but not limited to, corrosion inhibitors, non-emulsifiers, iron control agents, delay additives, silt suspenders, flowback additives, proppants, and gel breakers, can also be used in embodiments of the present invention. Other suitable additives useful in the present invention will be apparent to those of skill in the art and are to be considered within the scope of the present invention.

EXAMPLES

The following examples describe the preferred embodiments of the present invention. Other embodiments within the scope of the claims will be apparent to one skilled in the art from the consideration of the specification or practice of the invention disclosed herein.

Example 1

Figure 3:
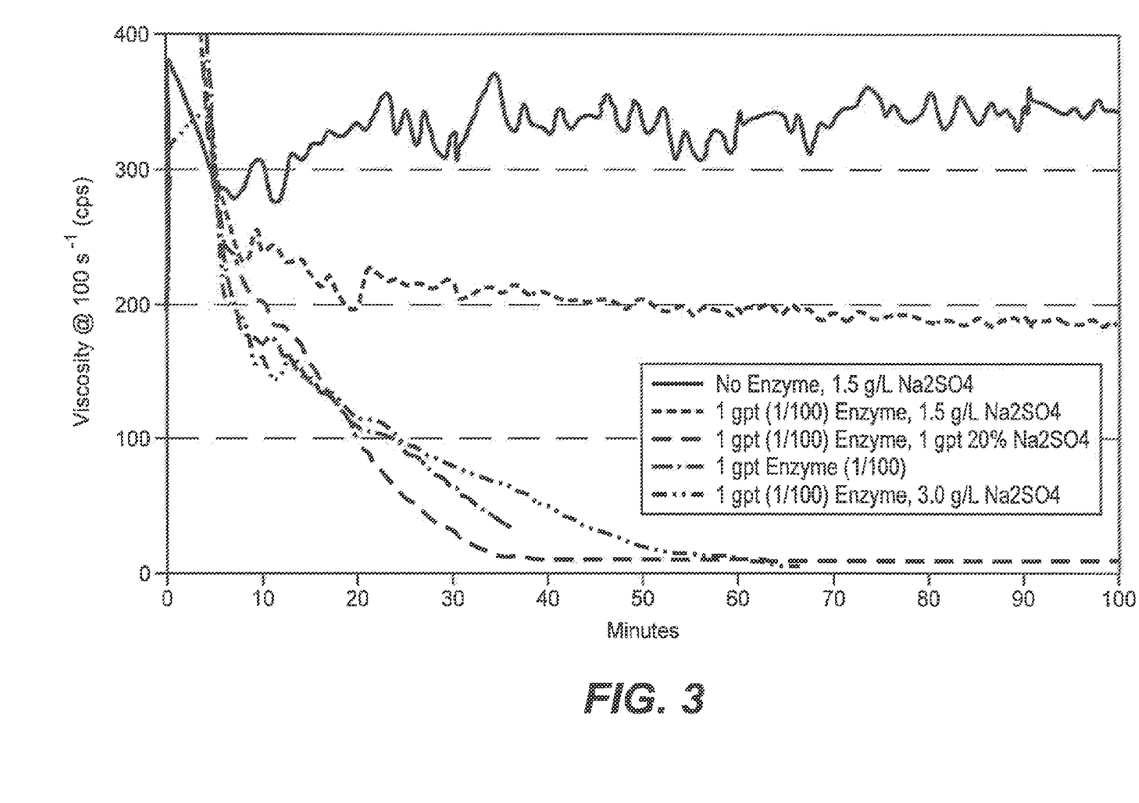
FIG. 3 represents the reduction in the viscosity of crosslinked guar polymer by the action of an enzyme breaker.

A solution was made comprising: 17 ppt of guar polymer, GW-3LDF; 1 gpt of clay stabilizer, Claytreat-3C; 1.5 gpt of buffer, BF-7L; 1 gpt of crosslinking agent, XLW-32; 1 gpt mannanohydrolase, GBW-22C, diluted 1/100 with distilled water; and 1 gpt of a 1% wt. solution of $Na_2SO_4$ (all components available from Baker Hughes Inc.). The solution was mixed with an overhead stirrer. 52 mL of crosslinked fluid was loaded on to a Chandler HTHP 5500 Viscometer and run at 500 psi, 150° F., and 100 $s^{-1}$ for an hour. As shown in FIG. 3, the addition of a small amount of $Na_2SO_4$ drastically improves the activity of the mannanohydrolase enzyme against the guar polymer. Moreover, there does not appear to be a difference between the activity of the enzyme in high concentrations of the effector (3 g/L) versus smaller concentrations of the effector (1 gpt 20% wt. $Na_2SO_4$ or 2 mg/L).

Example 2

Figure 4:
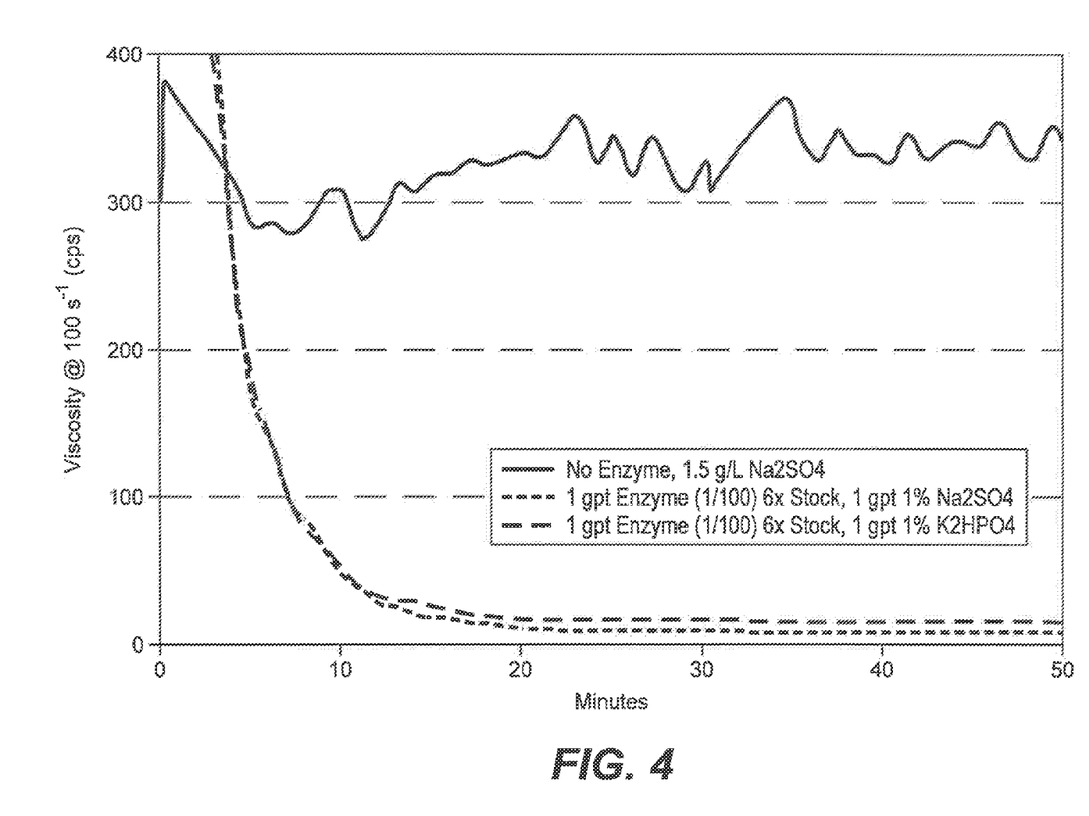
FIG. 4 represents the comparison of the effects of $SO_4^{2-}$ and $PO_4^{3-}$ on mannanohydrolase activity.

To compare the effects of phosphate and sulfate a solution was made comprising: 17 ppt of guar polymer, GW-3LDF; 1 gpt of clay stabilizer, Claytreat-3C; 1.5 gpt of buffer, BF-7L; 1 gpt of crosslinking agent, XLW-32; 1 gpt mannanohydrolase, GBW-22C, diluted 1/100 with distilled water; and 1 gpt of a 1% wt. solution of $K_2HPO_4$ (all components available from Baker Hughes Inc.). As can be seen from FIG. 4, both $SO_4^{2-}$ and $PO_4^{3-}$ provide similar effects on mannanohydrolase enzyme activity.

Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

What is claimed is:

1. A method of fracturing a subterranean formation comprising introducing into the formation an aqueous fracturing fluid comprising:
   a. a hydratable polymer selected from the group consisting of guar, guar derivatives, cellulose derivatives, water soluble biopolymers, and combinations thereof;
   b. a crosslinking agent for crosslinking the hydratable polymer to form a polymer gel;
   c. an enzyme breaker having an allosteric binding site and comprising at least one of the following:
      i. a mannanohydrolase enzyme that is coded by the nucleotide sequence shown in FIG. 1A, or a nucleotide sequence which is at least 60% homologous with the sequence of FIG. 1A, or when translated, has the amino acid sequence which is at least 60% homologous to the amino acid sequence of FIG. 1B;
      ii. an alkaline mannanohydrolase enzyme that is coded by the nucleotide sequence shown in FIG. 2, or a nucleotide sequence which is at least 60% homologous with the sequence of FIG. 2; or
      iii. a mannanohydrolase enzyme that is a member of the glycosyl hydrolase family 5 and is coded for by a gene sequence as depicted in FIG. 2; and
   d. an allosteric activator capable of binding to the allosteric binding site of the enzyme breaker, wherein the allosteric activator is selected from the group consisting of sulfates and phosphates.

2. The method of claim 1, wherein the hydratable polymer is guar or a guar derivative.

3. The method of claim 2, wherein the allosteric activator is sulfate is an alkali metal sulfate or an alkaline earth metal sulfate.

4. The method of claim 3, wherein the allosteric activator is sodium sulfate.

5. The method of claim 2, wherein the allosteric activator is soluble in water or brine.

6. The method of claim 2, wherein the allosteric activator is an alkali metal phosphate or an alkaline earth metal phosphate.

7. The method of claim 6, wherein the phosphate is potassium phosphate.

8. The method of claim 2, wherein the crosslinking agent contains boron or is capable of providing boron ions to the fluid.

9. The method of claim 2, wherein the hydratable polymer in the aqueous fracturing fluid has an intrinsic viscosity greater than about 14 dl/g.

10. The method of claim 9, wherein the intrinsic viscosity of the hydratable polymer in the aqueous fracturing fluid is greater than about 16 dl/g.

11. The method of claim 2, wherein the allosteric activator is in about a 1:1 stoichiometric ratio with the enzyme breaker.

12. The method of claim 1, wherein the enzyme breaker is a mannanohydrolase enzyme coded by the nucleotide sequence shown in FIG. 1A, or a nucleotide sequence which is at least 60% homologous with the sequence of FIG. 1A, or when translated, has the amino acid sequence which is at least 60% homologous to the amino acid sequence of FIG. 1B.

13. The method of claim 12, wherein the hydratable polymer is guar or a guar derivative.

14. The method of claim 13, wherein the allosteric activator is an alkali metal sulfate, an alkaline earth metal sulfate, an alkali metal phosphate or an alkaline earth metal phosphate.

15. The method of claim 13, wherein the allosteric activator is sodium sulfate.

16. The method of claim 13, wherein the allosteric activator is potassium phosphate.

17. The method of claim 13, wherein the crosslinking agent contains boron or is capable of providing boron ions to the fluid.

18. The method of claim 13, wherein the hydratable polymer in the aqueous fracturing fluid has an intrinsic viscosity greater than about 14 dl/g.

19. The method of claim 18, wherein the intrinsic viscosity of the hydratable polymer in the aqueous fracturing fluid is greater than about 16 dl/g.

20. An aqueous fracturing fluid comprising:
   a. a hydratable polymer selected from the group consisting of guar, guar derivatives, cellulose derivatives, water soluble biopolymers, and combinations thereof;
   b. a crosslinking agent for crosslinking the hydratable polymer to form a polymer gel;
   c. an enzyme breaker having an allosteric binding site and comprising at least one of the following:
      i. a mannanohydrolase enzyme that is coded by the nucleotide sequence shown in FIG. 1A, or a nucleotide sequence which is at least 60% homologous with the sequence of FIG. 1A, or when translated, has the amino acid sequence which is at least 60% homologous to the amino acid sequence of FIG. 1B;
      ii. an alkaline mannanohydrolase enzyme that is coded by the nucleotide sequence shown in FIG. 2, or a nucleotide sequence which is at least 60% homologous with the sequence of FIG. 2; or
      iii. a mannanohydrolase enzyme that is a member of the glycosyl hydrolase family 5 and is coded for by a gene sequence as depicted in FIG. 2; and
   d. an allosteric activator capable of binding to the allosteric binding site of the enzyme breaker, wherein the allosteric activator is selected from the group consisting of sulfates and phosphates.

21. The aqueous fracturing fluid of claim 20, wherein the hydratable polymer is guar or a guar derivative.

22. The aqueous fracturing fluid of claim 21, wherein at least one of the following conditions prevail:
   a. the allosteric activator is an alkali metal sulfate or an alkaline earth metal sulfate;
   b. the allosteric activator is an alkali metal phosphate or an alkaline earth metal phosphate; or
   c. the allosteric activator is soluble in water or brine.

23. The aqueous fracturing fluid of claim 20, wherein the crosslinking agent contains boron or is capable of providing boron ions to the fluid.

24. A method of fracturing a subterranean formation comprising introducing into the formation an aqueous fracturing fluid comprising:
   a) a hydratable polymer selected from the group consisting of guar, guar derivatives, cellulose derivatives, water soluble biopolymers, and combinations thereof;
   b) a crosslinking agent for crosslinking the hydratable polymer to form a polymer gel;
   c) an enzyme breaker having an allosteric binding site comprising at least one of the following:
      (i) a mannanohydrolase enzyme that is coded by the nucleotide sequence shown in FIG. 1A, or a nucleotide sequence which is at least 60% homologous with the sequence of FIG. 1A, or when translated, has the amino acid sequence which is at least 60% homologous to the amino acid sequence of FIG. 1B;
      (ii) a mannanohydrolase enzyme that is coded by the nucleotide sequence shown in FIG. 2, or a nucleotide sequence which is at least 60% homologous with the sequence of FIG. 2; or
      (iii) an mannanohydrolase enzyme that is a member of the glycosyl hydrolase family 5 and is coded for by a gene sequence as depicted in FIG. 2; and
   d) an allosteric activator selected from the group consisting of sulfates and phosphates; and
enhancing the activity of the enzyme breaker by binding the allosteric activator to the allosteric binding site of the enzyme breaker.

25. The method of claim 24, wherein the hydratable polymer is guar or a guar derivative.

26. The method of claim 25, wherein the sulfate is an alkali metal sulfate or an alkaline earth metal sulfate or the phosphate is an alkali metal phosphate or an alkaline earth metal phosphate.

* * * * *

UNITED STATES PATENT AND TRADEMARK OFFICE
CERTIFICATE OF CORRECTION

| | | |
|---|---|---|
| PATENT NO. | : 8,833,457 B2 | Page 1 of 1 |
| APPLICATION NO. | : 13/043349 | |
| DATED | : September 16, 2014 | |
| INVENTOR(S) | : Charles David Armstrong et al. | |

It is certified that error appears in the above-identified patent and that said Letters Patent is hereby corrected as shown below:

In the Claims

Col. 16 lines 56-58 Claim 3 should read: - The method of claim 2, wherein the allosteric activator is an alkali metal sulfate or an alkaline earth metal sulfate. -

Signed and Sealed this
Twenty-third Day of December, 2014

Michelle K. Lee
*Deputy Director of the United States Patent and Trademark Office*

SEQUENCE LISTING

```
<160> NUMBER OF SEQ ID NOS: 4

<210> SEQ ID NO 1
<211> LENGTH: 1053
<212> TYPE: DNA
<213> ORGANISM: Caldocellum Saccharolyticum
<220> FEATURE:
<221> NAME/KEY: CDS
<222> LOCATION: (7)..(1044)

<400> SEQUENCE: 1 ggatcc atg cgc ctg aaa acc aaa atc cgc aaa aag tgg ctg tca gtg         48
       Met Arg Leu Lys Thr Lys Ile Arg Lys Lys Trp Leu Ser Val
       1               5                  10 ctg tgc act gta gtc ttt ctg ctg aat att ctg ttt att gcg aac gtt        96
Leu Cys Thr Val Val Phe Leu Leu Asn Ile Leu Phe Ile Ala Asn Val
15                  20                  25                  30 acc atc ctg cca aaa gta ggc gcg gct acc tcc aac gat ggt gtg gtt       144
Thr Ile Leu Pro Lys Val Gly Ala Ala Thr Ser Asn Asp Gly Val Val
                35                  40                  45 aaa att gat acc tcg acc ctg att ggt acc aat cat gct cat tgc tgg       192
Lys Ile Asp Thr Ser Thr Leu Ile Gly Thr Asn His Ala His Cys Trp
            50                  55                  60 tat cgc gat cgt ctg gat acc gcg ctg cgc gga att cgt agt tgg ggt       240
Tyr Arg Asp Arg Leu Asp Thr Ala Leu Arg Gly Ile Arg Ser Trp Gly
        65                  70                  75 atg aac tcg gta cgc gtc gtt ctg tct aat ggc tat cgc tgg aca aaa       288
Met Asn Ser Val Arg Val Val Leu Ser Asn Gly Tyr Arg Trp Thr Lys
80                  85                  90 att ccg gcc agc gaa gtt gcc aac att att tcg ctg tcc cgc tcc ctg       336
Ile Pro Ala Ser Glu Val Ala Asn Ile Ile Ser Leu Ser Arg Ser Leu
95                  100                 105                 110 ggc ttc aaa gcc att att ctg gag gtg cat gat acc acc ggt tac ggt       384
Gly Phe Lys Ala Ile Ile Leu Glu Val His Asp Thr Thr Gly Tyr Gly
                115                 120                 125 gaa gat ggt gcg gcg tgc tcc ctg gca cag gca gtt gaa tat tgg aaa       432
Glu Asp Gly Ala Ala Cys Ser Leu Ala Gln Ala Val Glu Tyr Trp Lys
            130                 135                 140 gag atc aaa agc gtg ctg gat ggc aat gaa gat ttt gtc atc atc aat       480
Glu Ile Lys Ser Val Leu Asp Gly Asn Glu Asp Phe Val Ile Ile Asn
        145                 150                 155 att ggt aat gaa ccg tat ggt aat aac tat cag aac tgg gta aat           528
Ile Gly Asn Glu Pro Tyr Gly Asn Asn Tyr Gln Asn Trp Val Asn
    160                 165                 170 gat act aag aat gca att aaa gcg ctg cgc gat gcc ggc ttt aag cat       576
Asp Thr Lys Asn Ala Ile Lys Ala Leu Arg Asp Ala Gly Phe Lys His
175                 180                 185                 190 acc atc atg gta gat gcg ccg aac tgg ggc cag gat tgg tcg aat acc       624
Thr Ile Met Val Asp Ala Pro Asn Trp Gly Gln Asp Trp Ser Asn Thr
                195                 200                 205 atg cgc gac aat gct cag tct att atg gaa gcc gat cca ctg cgt aat       672
Met Arg Asp Asn Ala Gln Ser Ile Met Glu Ala Asp Pro Leu Arg Asn
            210                 215                 220 ctg gta ttt agc att cac atg tac ggt gtc tat aat act gcg agc aaa       720
Leu Val Phe Ser Ile His Met Tyr Gly Val Tyr Asn Thr Ala Ser Lys
        225                 230                 235 gtg gaa gaa tat atc aaa agt ttt gtg gat aaa ggt ctg ccg ctg gtt       768
```

-continued

```
                Val Glu Glu Tyr Ile Lys Ser Phe Val Asp Lys Gly Leu Pro Leu Val
                    240                 245                 250 atc ggc gaa ttc ggt cac cag cac act gat ggt gac cct gat gaa gag      816
Ile Gly Glu Phe Gly His Gln His Thr Asp Gly Asp Pro Asp Glu Glu
255                 260                 265                 270 gcg atc gtt cgc tat gcc aaa cag tat aaa att ggc ctg ttt agt tgg      864
Ala Ile Val Arg Tyr Ala Lys Gln Tyr Lys Ile Gly Leu Phe Ser Trp
                275                 280                 285 agt tgg tgt ggg aac agc agt tac gtc ggt tac ctg gat atg gtg aat      912
Ser Trp Cys Gly Asn Ser Ser Tyr Val Gly Tyr Leu Asp Met Val Asn
        290                 295                 300 aac tgg gac ccg aac aac ccg acc cca tgg ggg cag tgg tat aaa aca      960
Asn Trp Asp Pro Asn Asn Pro Thr Pro Trp Gly Gln Trp Tyr Lys Thr
    305                 310                 315 aat gcg atc ggc acg tca agc acg ccg acc ccg aca tcg act gtc acc     1008
Asn Ala Ile Gly Thr Ser Ser Thr Pro Thr Pro Thr Ser Thr Val Thr
320                 325                 330 cca acg cca ccg ccg cgc cag cac cag cat cgc caa taaaagctt           1053
Pro Thr Pro Pro Pro Arg Gln His Gln His Arg Gln
335                 340                 345
```

<210> SEQ ID NO 2
<211> LENGTH: 346
<212> TYPE: PRT
<213> ORGANISM: Caldocellum Saccharolyticum

<400> SEQUENCE: 2

```
Met Arg Leu Lys Thr Lys Ile Arg Lys Lys Trp Leu Ser Val Leu Cys
1               5                   10                  15

Thr Val Val Phe Leu Leu Asn Ile Leu Phe Ile Ala Asn Val Thr Ile
                20                  25                  30

Leu Pro Lys Val Gly Ala Ala Thr Ser Asn Asp Gly Val Val Lys Ile
            35                  40                  45

Asp Thr Ser Thr Leu Ile Gly Thr Asn His Ala His Cys Trp Tyr Arg
        50                  55                  60

Asp Arg Leu Asp Thr Ala Leu Arg Gly Ile Arg Ser Trp Gly Met Asn
65                  70                  75                  80

Ser Val Arg Val Val Leu Ser Asn Gly Tyr Arg Trp Thr Lys Ile Pro
                85                  90                  95

Ala Ser Glu Val Ala Asn Ile Ile Ser Leu Ser Arg Ser Leu Gly Phe
            100                 105                 110

Lys Ala Ile Ile Leu Glu Val His Asp Thr Thr Gly Tyr Gly Glu Asp
        115                 120                 125

Gly Ala Ala Cys Ser Leu Ala Gln Ala Val Glu Tyr Trp Lys Glu Ile
    130                 135                 140

Lys Ser Val Leu Asp Gly Asn Glu Asp Phe Val Ile Ile Asn Ile Gly
145                 150                 155                 160

Asn Glu Pro Tyr Gly Asn Asn Asn Tyr Gln Asn Trp Val Asn Asp Thr
                165                 170                 175

Lys Asn Ala Ile Lys Ala Leu Arg Asp Ala Gly Phe Lys His Thr Ile
            180                 185                 190

Met Val Asp Ala Pro Asn Trp Gly Gln Asp Trp Ser Asn Thr Met Arg
        195                 200                 205

Asp Asn Ala Gln Ser Ile Met Glu Ala Asp Pro Leu Arg Asn Leu Val
    210                 215                 220

Phe Ser Ile His Met Tyr Gly Val Tyr Asn Thr Ala Ser Lys Val Glu
225                 230                 235                 240
```

```
Glu Tyr Ile Lys Ser Phe Val Asp Lys Gly Leu Pro Leu Val Ile Gly
                245                 250                 255

Glu Phe Gly His Gln His Thr Asp Gly Asp Pro Asp Glu Glu Ala Ile
            260                 265                 270

Val Arg Tyr Ala Lys Gln Tyr Lys Ile Gly Leu Phe Ser Trp Ser Trp
        275                 280                 285

Cys Gly Asn Ser Ser Tyr Val Gly Tyr Leu Asp Met Val Asn Asn Trp
    290                 295                 300

Asp Pro Asn Asn Pro Thr Pro Trp Gly Gln Trp Tyr Lys Thr Asn Ala
305                 310                 315                 320

Ile Gly Thr Ser Ser Thr Pro Thr Pro Thr Ser Thr Val Thr Pro Thr
                325                 330                 335

Pro Pro Pro Arg Gln His Gln His Arg Gln
                340                 345

<210> SEQ ID NO 3
<211> LENGTH: 1401
<212> TYPE: DNA
<213> ORGANISM: Artificial sequence
<220> FEATURE:
<223> OTHER INFORMATION: Caldocellum Saccharolyticum mannahyrdolase DNA
      codon optimized for expression in E. Coli
<220> FEATURE:
<221> NAME/KEY: CDS
<222> LOCATION: (7)..(1044)

<400> SEQUENCE: 3 ctcgag atg agc agc ggt ttt tat gtg gat ggt aac acc ctg tat gat         48
       Met Ser Ser Gly Phe Tyr Val Asp Gly Asn Thr Leu Tyr Asp
       1               5                  10 gcc aat ggt cag ccg ttt gtg atg aaa ggc att aac cat ggc cat gcc        96
Ala Asn Gly Gln Pro Phe Val Met Lys Gly Ile Asn His Gly His Ala
15                  20                  25                  30 tgg tat aaa gat acc gcg agc acc gcg att ccg gcg att gcc gaa cag       144
Trp Tyr Lys Asp Thr Ala Ser Thr Ala Ile Pro Ala Ile Ala Glu Gln
                35                  40                  45 ggt gcg aat acc atc cgc att gtg ctg agc gat ggt ggc cag tgg gaa       192
Gly Ala Asn Thr Ile Arg Ile Val Leu Ser Asp Gly Gly Gln Trp Glu
            50                  55                  60 aaa gat gat att gat acc gtg cgt gaa gtg atc gaa ctg gcg gaa cag       240
Lys Asp Asp Ile Asp Thr Val Arg Glu Val Ile Glu Leu Ala Glu Gln
65                  70                  75 aat aaa atg gtg gcg gtg gtg gaa gtt cat gat gcg acc ggt cgc gat       288
Asn Lys Met Val Ala Val Val Glu Val His Asp Ala Thr Gly Arg Asp
            80                  85                  90 agc cgt agc gat ctg gat cgc gcg gtg gat tat tgg atc gaa atg aaa       336
Ser Arg Ser Asp Leu Asp Arg Ala Val Asp Tyr Trp Ile Glu Met Lys
95                  100                 105                 110 gat gcg ctg atc ggc aaa gaa gat acc gtg att att aat att gcg aac       384
Asp Ala Leu Ile Gly Lys Glu Asp Thr Val Ile Ile Asn Ile Ala Asn
                115                 120                 125 gaa tgg tat ggt agc tgg gat ggc gcg gcg tgg gcc gat ggc tat atc       432
Glu Trp Tyr Gly Ser Trp Asp Gly Ala Ala Trp Ala Asp Gly Tyr Ile
            130                 135                 140 gat gtg att ccg aaa ctg cgc gat gcg ggt ctg acc cat acc ctg atg       480
Asp Val Ile Pro Lys Leu Arg Asp Ala Gly Leu Thr His Thr Leu Met
        145                 150                 155 gtg gat gcg gcg ggt tgg ggc cag tat ccg cag agc att cat gat tat       528
Val Asp Ala Ala Gly Trp Gly Gln Tyr Pro Gln Ser Ile His Asp Tyr
    160                 165                 170
```

```
ggt cag gat gtg ttc aat gcc gat ccg ctg aaa aac acc atc ttt agc      576
Gly Gln Asp Val Phe Asn Ala Asp Pro Leu Lys Asn Thr Ile Phe Ser
175                 180                 185                 190 att cat atg tat gaa tat gcg ggc ggt gat gcg aat acc gtt cgc agc      624
Ile His Met Tyr Glu Tyr Ala Gly Gly Asp Ala Asn Thr Val Arg Ser
                195                 200                 205 aat atc gat cgt gtg atc gat cag gat ctg gcc ctg gtt att ggc gaa      672
Asn Ile Asp Arg Val Ile Asp Gln Asp Leu Ala Leu Val Ile Gly Glu
            210                 215                 220 ttc ggc cat cgt cat acc gat ggc gat gtg gat gaa gat acc att ctg      720
Phe Gly His Arg His Thr Asp Gly Asp Val Asp Glu Asp Thr Ile Leu
        225                 230                 235 agc tat agc gaa gaa acc ggt acc ggc tgg ctg gcg tgg agc tgg aaa      768
Ser Tyr Ser Glu Glu Thr Gly Thr Gly Trp Leu Ala Trp Ser Trp Lys
    240                 245                 250 ggt aat agc gcg gaa tgg gat tat ctg gat ctg agc gaa gat tgg gcc      816
Gly Asn Ser Ala Glu Trp Asp Tyr Leu Asp Leu Ser Glu Asp Trp Ala
255                 260                 265                 270 ggc aat cac ctg acc gat tgg ggc aac cgt att gtg cat ggc gcg aac      864
Gly Asn His Leu Thr Asp Trp Gly Asn Arg Ile Val His Gly Ala Asn
                275                 280                 285 ggc ctg cag gaa acc agc aaa ccg agc acc gtt ttc acc gat gat aac      912
Gly Leu Gln Glu Thr Ser Lys Pro Ser Thr Val Phe Thr Asp Asp Asn
            290                 295                 300 ggt ggc gcg ccg gaa ccg ccg acc acc acc ctg tat gat ttt gaa          960
Gly Gly Ala Pro Glu Pro Pro Thr Thr Thr Leu Tyr Asp Phe Glu
        305                 310                 315 ggc agc acc cag ggc tgg cac ggc agc aac gtg atg ggc ggc ccg tgg     1008
Gly Ser Thr Gln Gly Trp His Gly Ser Asn Val Met Gly Gly Pro Trp
    320                 325                 330 agc gtg acc gaa tgg ggt gcg agc ggc aat tat agc ctgaaaggcg          1054
Ser Val Thr Glu Trp Gly Ala Ser Gly Asn Tyr Ser
335                 340                 345 atgtgaacct gagcagcaac agcagccacg aactgtatag cgaacagagc cgtaacctgc   1114
atggctatag ccagctgaac gcgaccgtgc gtcatgcgaa ctggggcaac ccgggcaatg   1174
gcatgaatgc ccgtctgtat gtgaaaaccg gcagcgatta tacctggtat agcggcccgt   1234
ttacccgcat caatagcagc aatagcggta ccaccctgag ctttgatctg aacaacatcg   1294
aaaatagcca tcacgtgcgc gaaattggcg ttcagtttag cgccgcggat aacagcagcg   1354
gccagaccgc gctgtatgtg gataatgtga ccctgcgtta atgatca                 1401
```

<210> SEQ ID NO 4
<211> LENGTH: 346
<212> TYPE: PRT
<213> ORGANISM: Artificial sequence
<220> FEATURE:
<223> OTHER INFORMATION: Synthetic Construct

<400> SEQUENCE: 4

```
Met Ser Ser Gly Phe Tyr Val Asp Gly Asn Thr Leu Tyr Asp Ala Asn
1               5                   10                  15

Gly Gln Pro Phe Val Met Lys Gly Ile Asn His Gly His Ala Trp Tyr
                20                  25                  30

Lys Asp Thr Ala Ser Thr Ala Ile Pro Ala Ile Ala Glu Gln Gly Ala
            35                  40                  45

Asn Thr Ile Arg Ile Val Leu Ser Asp Gly Gly Gln Trp Glu Lys Asp
        50                  55                  60
```

```
Asp Ile Asp Thr Val Arg Glu Val Ile Glu Leu Ala Glu Gln Asn Lys
65                  70                  75                  80

Met Val Ala Val Val Glu Val His Asp Ala Thr Gly Arg Asp Ser Arg
                85                  90                  95

Ser Asp Leu Asp Arg Ala Val Asp Tyr Trp Ile Glu Met Lys Asp Ala
            100                 105                 110

Leu Ile Gly Lys Glu Asp Thr Val Ile Ile Asn Ile Ala Asn Glu Trp
        115                 120                 125

Tyr Gly Ser Trp Asp Gly Ala Ala Trp Ala Asp Gly Tyr Ile Asp Val
    130                 135                 140

Ile Pro Lys Leu Arg Asp Ala Gly Leu Thr His Thr Leu Met Val Asp
145                 150                 155                 160

Ala Ala Gly Trp Gly Gln Tyr Pro Gln Ser Ile His Asp Tyr Gly Gln
                165                 170                 175

Asp Val Phe Asn Ala Asp Pro Leu Lys Asn Thr Ile Phe Ser Ile His
            180                 185                 190

Met Tyr Glu Tyr Ala Gly Gly Asp Ala Asn Thr Val Arg Ser Asn Ile
        195                 200                 205

Asp Arg Val Ile Asp Gln Asp Leu Ala Leu Val Ile Gly Glu Phe Gly
    210                 215                 220

His Arg His Thr Asp Gly Asp Val Asp Glu Asp Thr Ile Leu Ser Tyr
225                 230                 235                 240

Ser Glu Glu Thr Gly Thr Gly Trp Leu Ala Trp Ser Trp Lys Gly Asn
                245                 250                 255

Ser Ala Glu Trp Asp Tyr Leu Asp Leu Ser Glu Asp Trp Ala Gly Asn
            260                 265                 270

His Leu Thr Asp Trp Gly Asn Arg Ile Val His Gly Ala Asn Gly Leu
        275                 280                 285

Gln Glu Thr Ser Lys Pro Ser Thr Val Phe Thr Asp Asp Asn Gly Gly
    290                 295                 300

Ala Pro Glu Pro Pro Thr Thr Thr Thr Leu Tyr Asp Phe Glu Gly Ser
305                 310                 315                 320

Thr Gln Gly Trp His Gly Ser Asn Val Met Gly Gly Pro Trp Ser Val
                325                 330                 335

Thr Glu Trp Gly Ala Ser Gly Asn Tyr Ser
            340                 345
```